United States Patent
Ravaux et al.

(10) Patent No.: US 6,416,768 B1
(45) Date of Patent: Jul. 9, 2002

(54) COSMETIC AND/OR DERMATOLOGICAL COMPOSITION CONSISTING OF AN EMULSION OF THE OIL-IN-WATER TYPE FORMED FROM LIPID VESICLES DISPERSED IN AN AQUEOUS PHASE CONTAINING AT LEAST ONE HYDROPHILIC ACIDIC ACTIVE AGENT

(75) Inventors: Danielle Ravaux, Saint-Arnoult en Yvelines; Jean-Pierre Laugier, Antony, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/499,391

(22) Filed: Feb. 7, 2000

(30) Foreign Application Priority Data

Feb. 5, 1999 (FR) .............................. 99 01387

(51) Int. Cl.$^7$ ................................ A61K 7/00
(52) U.S. Cl. ..................................... 424/401
(58) Field of Search ................ 424/59, 62, 401, 424/450; 514/844–846

(56) References Cited

U.S. PATENT DOCUMENTS

| | | | |
|---|---|---|---|
| 4,818,521 A | 4/1989 | Tamabuchi | 424/62 |
| 5,531,993 A | 7/1996 | Griat | 424/401 |
| 5,585,109 A | 12/1996 | Hayward et al. | 424/450 |
| 5,925,364 A * | 7/1999 | Ribier et al. | 424/401 |

FOREIGN PATENT DOCUMENTS

| | | |
|---|---|---|
| DE | 42 38 779 | 5/1994 |
| DE | 197 22 405 | 12/1998 |
| EP | 0 679 387 | 11/1995 |
| EP | 0 705 593 | 4/1996 |
| EP | 0 729 746 | 9/1996 |
| EP | 0 755 673 | 1/1997 |
| EP | 0 771 557 | 5/1997 |
| WO | WO 99/36053 | 7/1999 |

OTHER PUBLICATIONS

Terao Mikio et al, Patent Abstracts Of Japan, Publication No. 56120612, Publication Date Sep. 22, 1981, Application No. 55024673, Application Date Feb. 27, 1980, vol. 5, No. 200.

Database WPI, Week 199125, Derwent publications Ltd., London, GB, AN 1991–183200, XP–002122916.

* cited by examiner

Primary Examiner—Jose' G. Dees
Assistant Examiner—Konata M. George
(74) Attorney, Agent, or Firm—Oblon, Spivak, McClelland, Maier & Neustadt, P.C.

(57) ABSTRACT

A composition for topical use, comprising an oil-in-water emulsion formed from lipid vesicles consisting of oily globules, each having a lamellar liquid crystal coating obtained from at least one surfactant, dispersed in an aqueous phase containing at least one hydrophilic acidic active agent but which does not contain a gelling agent.

28 Claims, 1 Drawing Sheet

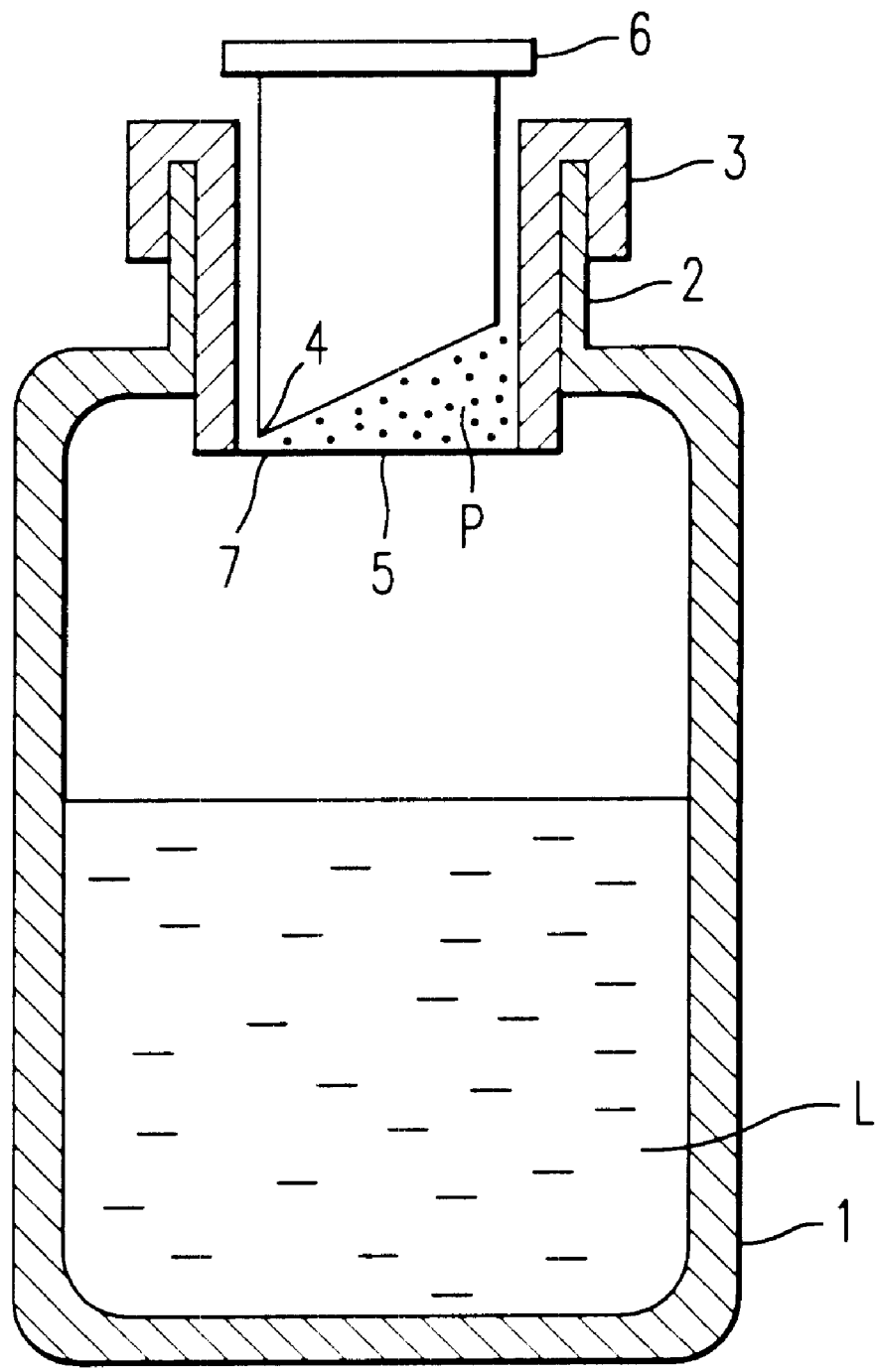

COSMETIC AND/OR DERMATOLOGICAL COMPOSITION CONSISTING OF AN EMULSION OF THE OIL-IN-WATER TYPE FORMED FROM LIPID VESICLES DISPERSED IN AN AQUEOUS PHASE CONTAINING AT LEAST ONE HYDROPHILIC ACIDIC ACTIVE AGENT

BACKGROUND OF THE INVENTION

1. Field of the Invention

The present invention relates to a cosmetic and/or dermatological composition for topical use comprising an emulsion of the oil-in-water type formed from lipid vesicles dispersed in an aqueous phase containing at least one hydrophilic acidic active agent.

2. Description of the Background

It is known practice to introduce various active agents, which are intended to impart specific treatments to the skin and/or the hair, into cosmetic compositions. However, some of these active agents have the drawback of being unstable in aqueous media and of degrading readily on contact with the skin. Thus, they rapidly lose their activity over time and this instability runs counter to the desired efficacy.

A desired objective for a long time has been to formulate the likes of ascorbic acid or vitamin C, on account of its many beneficial properties, stably into a topical formulation. Ascorbic acid stimulates the synthesis of connective tissue and, in particular, of collagen. It reinforces the skin tissues' defense against external attacking factors such as ultraviolet radiation and atmospheric pollutants; it compensates for vitamin E deficiency in the skin; it depigments the skin; and it has a free-radical-scavenging function. These last two properties make it an excellent candidate as a cosmetic or dermatological active agent for combating ageing of the skin or for preventing such ageing. Unfortunately, because of its chemical structure (an α-keto lactose), ascorbic acid is highly sensitive to certain environmental parameters such as light, oxygen and water. Thus, ascorbic acid in ascorbic acid containing formulations frequently degrades when the formulations are exposed to these environmental parameters.

Several solutions have thus been suggested in the prior art for reducing and/or delaying the degradation of ascorbic acid in various preparations.

EP 0 679 387 discloses a composition comprising a hydrophilic support and ascorbic acid in pulverulent form. These ingredients are intended to be mixed together at the time of use. The support is described as comprising an aqueous medium and at least one hydrophilic gelling agent and as being capable of tolerating the introduction of an acidic compound. To do this, the gelling agent can be selected from polysaccharides, synthetic polymers and celluloses. A buffer is added to the solution so that the final pH of the composition is greater than 3.8.

Moreover, EP 0 642 781 discloses an emulsion of the oil-in-water type having a pH of less than 3.5, comprising, as stabilizer, a crosslinked anionic copolymer prepared by copolymerizing (i) acrylamide, (ii) 2-acrylamidomethylpropanesulfonic acid (AMPS), and (iii) at least one compound containing olefinic polyunsaturation as monomer components. The publication indicates that, at higher concentrations, the copolymer also exerts an emulsion-thickening function, such that the emulsion is presented as being able to have various fluidities ranging from that of milk to that of cream.

Finally, EP 0 755 673 discloses a topical composition comprising at least one water-sensitive active agent, such as ascorbic acid, stabilized with a combination of at least one polyol and at least one structuring agent selected from (meth)acrylic polymers and oils. The polyol, which is selected, for example, from propylene glycol, polyethylene glycol and glycerol, is present in an amount which is sufficient to impart a water activity value for the composition of less than or equal to 0.85.

These compositions of the prior art, which are formulated to stabilize ascorbic acid, have the drawback of being insufficiently viscous, or even insufficiently stable, at acidic pH, in particular, at a pH of from 2 to 4. It is thought that by maintaining the composition within this pH range, it is ensured that a large portion of the ascorbic acid will remain in protonated, uncharged form, in which form the penetration of the molecule into the skin is supposed to be facilitated. Furthermore, the large amount of polyol in the composition described in EP 755 673 imparts a relatively greasy feel to the composition, which certain users may find objectionable.

The low viscosity and/or stability of the known compositions containing ascorbic acid and which comprise a cosmetic gelling agent is very much such that, when the pH values of the compositions decrease down to a value ranging from 2 to 4, the ionic gelling agents the compositions contain undergo changes in their three-dimensional network. A variation in the van der Waals forces is also observed, implying nonionic gelling agents. The result of these changes is a reduction in the gelling power of these compounds, such that the emulsion containing these gelling agents transitions from having a creamy texture to the texture of a fluid such as a milk, or even such that the aqueous and oily phases of the emulsion separate, in extreme cases. The separation of the emulsion can be more or less gradual and/or more or less complete, depending on the case.

Other compositions of the prior art containing a hydrophilic, acidic active agent and a cosmetic gelling agent, and which thus pose the same problems of low viscosity and/or stability at acidic pH, are those described in FR-A-2 680 685 and EP 705 593. These are oil-in-water emulsions in which the oily phase is formed from lipid spheroids and in which the aqueous phase, gelled with a compound of the carbomer or xanthan gum type, contains, for example, a UV screening agent containing a sulfonic acid function. These compositions furthermore have the drawback that the lipid spheroids they contain are solid particles which are perceptible to the touch and have a particle size of 100 to 5000 μm. The spheroids thus have a tendency, on account of their size, to become crushed on the surface of the skin, leading to mediocre penetration of the active agents they contain. A need, therefore, continues to exist for a composition, particularly for topical application, which provides enhanced stability for active agents susceptible to degradation over time.

SUMMARY OF THE INVENTION

Accordingly, one object of the present invention is to provide a composition containing an acidic active agent and which has a viscosity greater than 500 centipoise at acidic pH, preferably at a pH of 2 to 4.

Another object of the present invention is to provide a composition containing an acidic active agent and which has good cosmetic properties, in particular, a non-greasy feel.

Still another object of the invention is to provide a composition having a water activity value of greater than 0.90, preferably greater than 0.95.

Briefly, these objects and other objects of the present invention as hereinafter will become more readily apparent can be attained by a composition for topical use, comprising an oil-in-water emulsion formed from lipid vesicles consisting of oily globules, each having a lamellar liquid crystal coating obtained from at least one surfactant, dispersed in an aqueous phase containing at least one hydrophilic acidic active agent but which does not contain a gelling agent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

the Figure is a diagram of a packaging and application device for the treatment of the skin with the composition of the present invention.

DETAILED DESCRIPTION OF THE PREFERRED EMBODIMENTS

It has now been discovered that the use of vesicles in the form of lamellar phases in compositions in which the aqueous phase contains an acidic active agent, such as ascorbic acid, and is free of gelling agent, makes it possible to achieve the objective of the present invention.

One aspect of the present invention is a composition for topical use, comprising an emulsion of the oil-in-water type formed from lipid vesicles dispersed in an aqueous phase containing at least one hydrophilic acidic active agent, the vesicles consisting of oily globules each having a lamellar liquid crystal coating obtained from at least one surfactant. The aqueous phase contains no gelling agent.

The composition of the invention has a viscosity greater than 500 centipoises. In the context of this description, the viscosities indicated are those measured at T=10 seconds on a Rheomat RM 180 machine from Mettler at 25° C., under atmospheric pressure, at 200 rpm, using a measuring body of the anchor type referred to as a "rotor", i.e. rotor No. 3 supplied with the machine in the case of creams (containing the emulsion and the acidic active agent) and rotor No. 1 in the case of milks (containing the emulsion without acidic active agent). The measurements read on the machine are converted into centipoises upon reference to a curve supplied by the manufacturer.

The acidic active agent can be selected from hydrophilic organic acids such as α-hydroxy acids, β-hydroxy acids and α-keto acids, optionally in lactone form, and inorganic acids such as phosphoric acid. The acidic active agent can also be selected from the group consisting of kojic acid, caffeic acid, physic acid, quinic acid and benzene-1,4bis(3-methylidenecamphorsulfonic acid).

The acidic active agents preferably used are glycolic acid, lactic acid, mandelic acid, malic acid, tartaric acid, citric acid, hydroxybutyric acid, gluconic acid, ascorbic acid, salicylic acid, gentisic acid, homogentisic acid and pyruvic acid. Ascorbic acid is preferably used.

The acidic active agent is present in the composition of the invention in an amount which is sufficient to achieve the desired effects, and which represents, for example, from 0.1 to 10% of the total weight of the composition.

The vesicles employed in the composition of the invention comprise oily globules each having a lamellar liquid crystal coating.

According to one preferred embodiment, the oily globules comprise at least one lipophilic active agent. Thus, the oily globules can comprise an active agent selected, for example, from antioxidants, free-radical scavengers, moisturizers, melanin regulators, tanning accelerators, depigmenting agents, skin-coloring agents, liporegulators, weight-reduction agents, anti-acne agents, antiseborrhoeic agents, antiageing agents, anti-wrinkle agents, anti-UV agents, keratolytic agents, anti-inflammatory agents, refreshing agents, cicatrizing agents, vascular protection agents, antibacterial agents, antifungal agents, antiperspirants, deodorants, skin conditioners, immunomodulators, nourishing agents, anti-dandruff agents, agents for combating hair loss, hair dyes, hair bleaches, reducing agents for permanent-waving, hair conditioners, essential oils and fragrances.

Suitable Examples of lipophilic active agents for treating the skin and/or the hair, which can be used in the context of the present invention, include D-α-tocopherol, DL-α-tocopherol, D-α-tocopheryl acetate, DL-α-tocopheryl acetate, ascorbyl palmitate, vitamin F glycerides, D vitamins, retinol, retinol esters, β-carotene, D-panthenol, farnesol, farnesyl acetate, oils rich in 5 essential fatty acids, 5-n-octanoylsalicylic acid, salicylic acid, alkyl esters of α-hydroxy acids, asiatic acid, madecassic acid, asiaticoside, total extract of Centella asiatica, β-glycyrrhetinic acid, α-bisabolol, ceramides, phytanetriol, sphingomyelin from milk, phospholipids of marine origin which are rich in polyunsaturated essential fatty acids, ethoxyquine, extract of rosemary, extract of balm, quercetin, extract of dried microalgae, essential oil of bergamot, octyl methoxycinnamate, butylmethoxydibenzoylmethane, octyltriazone, 3,5-di-tert-butyl-4-hydroxy-3-benzylidenecamphor, 2-benzotriazol-2-yl-4-methyl-6-[3-[1,3,3,3-tetramethyl-1[trimethylsilyl)oxy]disiloxanyl]-2-methylpropyl]phenol, perfluoro oil and hyperoxygenated corn oil.

The oily globules can also contain various additional additives such as oils, waxes or gums having, for example, emollient or lubricant properties.

The coated oily globules advantageously have an average diameter of less than 1000 nanometres, preferably less than 500 nanometres and better still less than 200 nanometres.

The lamellar liquid crystal coating on the oily globules can be produced, according to a first embodiment, from at least one lipophilic surfactant, from at least one hydrophilic surfactant and from at least one ionic amphiphilic lipid. The relative amounts of the lipophilic surfactant, hydrophilic surfactant and ionic amphiphilic lipid preferably vary within the following respective ranges: 35–55%/25–40%/15–35% by weight relative to their total weight. A process for preparing such vesicles is described in EP 0 705 593.

In a second embodiment of the invention, the lamellar liquid crystal coating can be produced from at least one lipophilic surfactant, from at least one hydrophilic surfactant and from at least one fatty acid. In this case, the aqueous phase contains at least one basic agent in dissolved form. The relative amounts of lipophilic surfactant, hydrophilic surfactant and fatty acid preferably vary within the following respective ranges: 35–55%/25–40%/15–35% by weight relative to their total weight. A process for preparing such vesicles is described in EP 0 641 557.

Preferably, the lipophilic surfactant and the hydrophilic surfactant each comprise at least one saturated fatty chain containing more than 12 carbon atoms approximately, preferably from 16 to 22.

In addition, the lipophilic surfactant advantageously has an HLB (hydrophilic-lipophilic balance) of 2 to 5. Suitable Examples of lipophilic surfactants with an HLB of 2 to 5 include sucrose distearate, diglyceryl distearate, tetraglyceryl tristearate, decaglyceryl decastearate, diglyceryl monostearate, hexaglyceryl tristearate, decaglyceryl-5-pentastearate sorbitan monostearate, sorbitan tristearate, diethylene glycol monostearate, the ester of glycerol and of palmitic acid and stearic acid, the monostearate polyoxyethylenated with 2 EO (comprising 2 ethylene oxide units), glyceryl mono- and dibehenate, and pentaerythrityl tetrastearate.

With respect to the hydrophilic surfactant, it advantageously has an HLB of 8 to 12. Suitable Examples of hydrophilic surfactants with an HLB of 8 to 12 include sorbitan monostearate polyoxyethylenated with 4 EO, sorbitan tristearate polyoxyethylenated with 20 EO, the monostearate polyoxyethylenated with 8 EO, hexaglyceryl monostearate, the monostearate polyoxyethylenated with 10 EO, the distearate polyoxyethylenated with 12 EO, and methylglucose distearate polyoxyethylenated with 20 EO.

The ionic amphiphilic lipid can be a neutralized anionic lipid, amphoteric lipid or alkylsulfonic derivative. For example, the ionic amphiphilic lipid can be selected from the group consisting of alkali metal salts of dicetyl phosphate, alkali metal salts of dimyristyl phosphate, alkali metal salts of cholesteryl sulfate, alkali metal salts of cholesteryl phosphate, the mono- and disodium salts of acylglutamic acids, phospholipids, alkylsulfonic derivatives of formula:

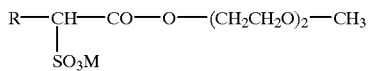

wherein R represents $C_{16}H_{33}$ and $C_{18}H_{37}$ radicals taken as a mixture or separately and M is an alkali metal.

The fatty acid can be selected from the group consisting of palmitic acid, stearic acid, arachidic acid and behenic acid.

The basic agent is dissolved in the aqueous phase in an amount at least equal to the amount required to neutralize the fatty acid. It can be selected from the group consisting of sodium hydroxide, triethanolamine, lysine and arginine.

The compositions of the invention can also contain various additional additives in the aqueous phase, such as preserving agents or sequestering agents.

The compositions are most commonly in the form of a milk or a cream, although other means of presentation are not excluded.

The composition of the invention can be in the form:
of an oil-in-water emulsion formed from lipid vesicles dispersed in an aqueous phase containing no gelling agent, the vesicles consisting of oily globules each having a lamellar liquid crystal coating obtained from at least one surfactant; and
of at least one acidic active agent in pulverulent form or in the form of an aqueous solution, which components are intended to be mixed together at the time of use.

In this case, the emulsion is packaged, for example, in a container closed by means of a stopper comprising the acidic active agent, a perforable and/or detachable separator being provided between the active agent and the emulsion.

The Figure shows, in schematic longitudinal section, an example of a light-proof, two compartment bottle containing the composition of the invention, before mixing the emulsion and the pulverulent active agent, such as to at least 99% pure ascorbic acid.

Specifically, the bottle is comprised of a body (1) made of a material which screens external light, and which acts as a reservoir for fluid emulsion (L). The emulsion (L) has a viscosity of less than 10 centipoise. At the top part, the reservoir (1) is provided with a neck (2) into which is inserted a cup (3), closed at the bottom part by means of an operculum (5), and the active agent (P) is placed inside the cup. The operculum (5) can be molded as a single item with the cup (3) and preferably comprises zones of weakness. As a variant, the operculum (5) can consist of an aluminum foil heat-welded onto the bottom of the cup.

In the open top part of the cup (3) is inserted, in a leak-tight manner, a trocar (6), the bottom part of which is provided with a cutting zone (4) which is capable of cutting the operculum (5). Before use, the cup (3) provided with its trocar (6) acts as a stopper for the container.

The assembly functions as follows.

The user pushes the trocar (6) into the cup (5), causing the operculum (5) to tear along its weakness lines, and the pulverulent active agent (P) flows into the fluid emulsion (L). Next, the assembly is shaken to dissolve the active agent in the emulsion, which then reaches a viscosity of at least 500 centipoise. The trocar (6) is then removed from the cup (3) to free the distribution orifice and optionally a soft plastic teat, pierced at its end, is placed onto the cup (3), so as to facilitate the release of the product onto the skin.

Other multi-compartment bottles which can be used to separately package the emulsion and the pulverulent active agent of the invention are, in particular, those described in EP 0 528 707, EP 0 230 195, FR 84/13355 and FR 85/17143, although this list is not limiting. The composition of the invention can be applied to the skin, body hair or head hair, depending on the use for which it is intended. It can thus be used in a cosmetic preparation and/or in a cosmetic treatment process for the skin which-consists in applying the composition of the invention to the skin, for example in order to tone it, to regenerate it, to smooth out the fine lines on the skin, and/or to combat the damage caused by UV radiation and/or to strengthen the skin tissues against attacking environmental factors.

As a variant, the composition of the invention can be used in a therapeutic treatment process, i.e. a process for manufacturing a dermatological preparation, such as a preparation intended to bleach and/or depigment the skin, body hair and/or head hair.

The present invention also relates to a process for preparing a composition containing a hydrophilic acidic active agent, the composition having a viscosity of greater than 500 centipoise at a pH ranging from 2 to 4, comprising the introduction of the active agent into an emulsion of the oil-in-water type formed from oily globules dispersed in an aqueous phase containing no gelling agent, the oily globules each having a lamellar liquid crystal coating obtained from at least one surfactant.

Obviously, numerous modifications and variations of the present invention are possible in light of the above teachings. It is, therefore, to be understood that within the scope of the appended claims, the invention may be practiced otherwise than as specifically described herein. Except where otherwise indicated, the amounts in the Examples are given as percentages by weight.

EXAMPLES

Example 1

The emulsion below is introduced into a two compartment bottle of the type illustrated in FIG. 1:

| | |
|---|---|
| Poly(2-glyceryl stearate) | 0.2 g |
| PEG-8 stearate | 0.135 g |
| Disodium salt of hydrogenated tallow and of L-glutamic acid | |
| (Amisoft HS-20 supplied by Ajinomoto) | 0.09 g |
| Isocetyl stearate | 0.7 g |
| Squalane | 1.3 g |
| Water | 7.075 g |
| TOTAL | 95 g |

The emulsion is in the form of a white fluid milk with a viscosity of about 7 centipoise at 25° C. and a pH of 7.3±0.3.

The bottle is crimped with a cap containing 0.5 g of ascorbic acid in the form of a white powder.

During the introduction of the pulverulent acid into the above emulsion, a reduction in the pH and a substantial increase in the viscosity are observed, until a composition with a viscosity of 850 centipoise at 25° C., with the appearance of a white cream, and with a pH of 3.3±0.3, is obtained.

After ten days at room temperature, no reduction in the amount of ascorbic acid present in solution (measured by high pressure liquid -chromatography) is observed. The pH of the cream has not changed.

Example 2

The emulsion below is introduced into a two-compartment bottle of the type illustrated in FIG. 1:

| | |
|---|---|
| Polysorbate 61 | 0.16 g |
| Stearic acid | 0.12 g |
| Stearyl alcohol | 0.11 g |
| Petroleum jelly | 0.3 g |
| Cholesterol | 0.005 g |
| Sucrose tristearate | 0.264 g |
| Isocetyl stearate | 0.5 g |
| Cyclopentasiloxane | 0.3 g |
| Water | 7.681 g |
| Triethanolamine | 0.06 g |
| TOTAL | 95 g |

The emulsion is in the form of a white fluid milk with a viscosity of about 6 centipoise at 25° C. and a pH of 7.7±0.3.

The bottle is crimped with a cap containing 0.5 g of ascorbic acid in the form of a white powder.

After introducing the pulverulent acid into the above emulsion, a white cream with a viscosity of 1300 centipoise at 25° C. and a pH of 3.5±0.3 is obtained.

After ten days at room temperature, the cream shows a very slight amount of release, which can be avoided by storing the cream at 4° C. instead. Its pH has not changed.

Example 3

The emulsion below is introduced into a two-compartment bottle of the type illustrated in FIG. 1:

| | |
|---|---|
| Poly(2-glyceryl stearate) | 0.2 g |
| PEG-8 stearate | 0.135 g |
| Disodium salt of hydrogenated tallow and of L-glutamic acid | |
| (Amisoft HS-20 supplied by Ajinomoto) | 0.09 g |
| Isocetyl stearate | 0.7 g |
| Squalane | 1.3 g |
| Water | 7.075 g |
| TOTAL | 9.5 g |

The emulsion is in the form of a white fluid milk with a viscosity of about 7 centipoise at 25° C. and a pH of 7.3.

A cap containing 0.5 g of pulverulent glycolic acid is crimped onto the bottle.

After introducing the pulverulent acid into the above emulsion, a white cream with a viscosity of 600 centipoise at 25° C. and a pH of 2.5 is obtained.

Example 4

The emulsion below is introduced into a two-compartment bottle of the type illustrated in FIG. 1:

| | |
|---|---|
| Polysorbate 61 | 0.16 g |
| Stearic acid | 0.12 g |
| Stearyl alcohol | 0.11 g |
| Petroleum jelly | 0.3 g |
| Cholesterol | 0.005 g |
| Sucrose tristearate | 0.264 g |
| Isocetyl stearate | 0.5 g |
| Cyclopentasiloxane | 0.3 g |
| Water | 7.681 g |
| Triethanolamine | 0.06 g |
| TOTAL | 9.5 g |

A cap containing 0.5 g of phosphoric acid as an 85% solution in water, intended to be mixed with the above emulsion at the time of use, is crimped onto the bottle.

Example 5

The emulsion below is introduced into the two-compartment bottle of the type illustrated in FIG. 1:

| | |
|---|---|
| Polysorbate 61 | 0.16 g |
| Stearic acid | 0.12 g |
| Stearyl alcohol | 0.11 g |
| Petroleum jelly | 0.3 g |
| Cholesterol | 0.005 g |
| Sucrose tristearate | 0.264 g |
| Isocetyl stearate | 0.5 g |
| Cyclopentasiloxane | 0.3 g |
| Water | 7.681 g |
| Triethanolamine | 0.06 g |
| TOTAL | 9.5 g |

A cap containing 0.5 g of lactic acid as a 90% solution in water is crimped onto the bottle. The lactic acid solution and the above emulsion are intended to be mixed together at the time of use to prepare a day cream.

Example 6

Measurement of the water activity value ($a_w$) of the composition

The water activity $a_w$ of a medium containing water is the ratio of the vapor pressure of water for the product, "$P_{H_2O}$ product", and the vapor pressure of pure water, "$P_{H2O}$ pure", at the same temperature. It can also be expressed as the ratio of the number of water molecules "$N_{H2O}$" to the total number of molecules "$N_{H2O}+N_{dissolved\ substances}$", which takes the dissolved substances "$N_{dissolved\ substances}$" into account.

$$a_w = \frac{P_{H2O} product}{P_{H2O} pure} = \frac{N_{H2O}}{N_{H2O} + N_{dissolved\ substances}}$$

Various methods can be used to measure the water activity. The most common is the manometric method, by which the vapor pressure is measured directly.

Results:

The water activity values for the creams of Examples 1 and 2 above were determined as being 0.988 and 0.991, respectively. These values reflect the good cosmetic properties of these creams, which lack the characteristic feel of the creams of the prior art stabilized with polyols.

The disclosure of French priority Application No. 9901387 filed Feb. 5, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A composition for topical use, comprising:
    an oil-in-water emulsion formed from lipid vesicles consisting of oily globules, each having a lamellar liquid crystal coating obtained from at least one surfactant, dispersed in an aqueous phase containing at least one hydrophilic acidic active agent but which does not contain a gelling agent,
    wherein said composition has a pH of 2 to 4 and a viscosity greater than 500 centipoise.

2. The composition according to claim 1, wherein the acidic active agent is a hydrophilic organic acid selected from the group consisting of α-hydroxy acids, β-hydroxy acids and α-keto acids optionally in lactone form, or an inorganic acid.

3. The composition according to claim 2, wherein the acidic active agent is selected from the group consisting of glycolic acid, lactic acid, mandelic acid, malic acid, tartaric acid, citric acid, hydroxybutyric acid, gluconic acid, ascorbic acid, salicylic acid, gentisic acid, homogentisic acid and pyruvic acid.

4. The composition according to claim 3, wherein the acidic active agent is ascorbic acid.

5. The composition according to claim 2, wherein the acidic active agent is selected from the group consisting of kojic acid, caffeic acid, physic acid, quinic acid and benzene-1,4-bis(3-methylidenecamphorsulfonic acid).

6. The composition according to claim 1, wherein the lamellar liquid crystal coating is prepared from at least one lipophilic surfactant, from at least one hydrophilic surfactant or from at least one ionic amphiphilic lipid.

7. The composition according to claim 1, wherein the lamellar liquid crystal coating is prepared from at least one lipophilic surfactant, from at least one hydrophilic surfactant or from at least one fatty acid, and the aqueous phase contains at least one basic agent in dissolved form.

8. The composition according to claim 6, wherein the lipophilic surfactant and the hydrophilic surfactant each comprise at least one saturated fatty chain containing more than approximately 12 carbon atoms.

9. The composition according to claim 6, wherein the lipophilic surfactant has an HLB (hydrophilic-lipophilic balance) ranging from 2 to 5.

10. The composition according to claim 9, wherein the lipophilic surfactant having an HLB ranging from 2 to 5 is selected from the group consisting of sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the ester of glycerol and of palmitic acid or stearic acid, the monostearate polyoxyethylenated with 2 EO (comprising 2 ethylene oxide units), glyceryl mono- or dibehenate, and pentaerythrityl tetrastearate.

11. The composition according to claim 6, wherein the hydrophilic surfactant has an HLB ranging from 8 to 12.

12. The composition according to claim 6, wherein the hydrophilic surfactant having an HLB ranging from 8 to 12 is selected from the group consisting of sorbitan monostearate polyoxyechylenated with 4 EO, sorbitan tristearate polyoxyethylenated with 20 EO, the monostearate polyoxyethylenated with 8 EO, hexaglyceryl monostearate, the monostearate polyoxyethylenated with 10 EO, the distearate polyoxyethylenated with 12 EO, and methylglucose distearate polyoxyethylenated with 20 EO.

13. The composition according to claim 6, wherein the ionic amphiphilic lipid is selected from the group consisting of neutralized anionic lipids, amphoteric lipids and alkylsulfonic derivatives.

14. The composition according to claim 6, wherein the ionic amphiphilic lipid is selected from the group consisting of alkali metal salts of dicetyl phosphate, alkali metal salts of dimyristyl phosphate, alkali metal salts of cholesterol sulphate, alkali metal salts of cholesterol phosphate, the mono and disodium salts of acylglutamic acids, phospholipids, alkylsulfonic derivatives of formula:

$$R-\underset{\underset{SO_3M}{|}}{CH}-CO-O-(CH_2CH_2O)_2-CH_3$$

wherein R represents $C_{16}H_{33}$ or $C_{18}H_{37}$ radicals taken as a mixture or separately and M is an alkali metal.

15. The composition according to claim 7, wherein the fatty acid is selected from the group consisting of palmitic acid, stearic acid, arachidic acid and behenic acid.

16. The composition according to claim 7, wherein the basic agent is dissolved in the aqueous phase in an amount at least equal to the amount required to neutralize the fatty acid.

17. The composition according to claim 7, wherein the basic agent is selected from the group consisting of sodium hydroxide, triethanolamine, lysine and arginine.

18. The composition according to claim 1, wherein the oily globules comprise at least one lipophilic active agent.

19. The composition according to claim 18, wherein the lipophilic active agent is selected from the group consisting of antioxidants, free-radical scavengers, moisturizers, melanin regulators, tanning accelerators, depigmenting agents, skin-coloring agents, liporegulators, weight-reduction agents, anti-acne agents, antiseborrhoeic agents, anti-ageing agents, anti-wrinkle agents, anti-UV agents, keratolytic agents, anti-inflammatory agents, refreshing agents, cicatrizing agents, vascular-protection agents, antibacterial agents, antifungal agents, antiperspirants, deodorants, skin conditioners, immunomodulators, nourishing agents, antidandruff agents, agents for combating hair loss, hair dyes, hair bleaches, reducing agents for permanent-waving, hair conditioners, essential oils and fragrances.

20. The composition according to claim 18, wherein the lipophilic active agent is selected from the group consisting of D-α-tocopherol, DL-α-tocopherol, D-α-tocopheryl acetate, DL-α-tocopheryl acetate, ascorbyl palmitate, vitamin F glycerides, D vitamins, retinal, retinal esters, β-carotene, D-panthenol, farnesol, farnesyl acetate, oils rich in essential fatty acids, 5-n-octanoylsalicylic acid, salicylic acid, alkyl esters of α-hydroxy acids, asiatic acid, madecassic acid, asiaticoside, total extract of Centella asiatica, β-glycyrrhetinic acid, α-bisabolol, ceramides, phytanetriol, sphingomyelin from milk, phospholipids of marine origin which are rich in polyunsaturated essential fatty acids, ethoxyquine, extract of rosemary, extract of balm, quercetin, extract of dried microalgae, essential oil of bergamot, octyl methoxycinnamate, -butylmethoxydibenzoylmethane, octyltriazone, 3,5-ditert-butyl-4-hydroxy-3-benzylidenecamphor, 2-benzatriazol-2-yl-4-methyl-6-[3-[1,3,3,3-tetramethyl-1[trimethylsilyl)oxy]disiloxanyl]-2-methylpropyl]phenol, perfluoro oil and hyperoxygenated corn oil.

21. The composition according to claim 1, wherein the acidic active agent represents from 0.1 to 10% of the total weight of the composition.

22. The composition according to claim 1, which is in the form of:
    an oil-in-water emulsion formed from lipid vesicles dispersed in an aqueous phase containing no gelling agent, the vesicles consisting of oily globules each having a lamellar liquid crystal coating obtained from at least one surfactant; and
    at least one acidic active agent in pulverulent form or in the form of an aqueous solution, wherein the two components are mixed together at the time of use.

23. The composition according to claim 22, wherein, with reference to the Figure, the emulsion (L) is packaged in a container (1) closed by a stopper (3) comprising the acidic active agent (P), a perforable and/or detachable separator (5) being provided between the active agent (P) and the emulsion (L).

24. The composition according to claim 22, wherein, before mixing with the acidic active agent, the emulsion has a viscosity of less than 10 centipoise.

25. A process for preparing a composition containing a hydrophilic acidic active agent, comprising:
    introducing the active agent into an oil-in-water emulsion from oily globules, each having a lamellar liquid crystal coating obtained from at least one surfactant, dispersed in an aqueous phase containing no gelling agent, said composition thereby having a viscosity of greater than 500 centipoise at a pH ranging from 2 to 4.

26. A method of preparing a cosmetic preparation, comprising:
    separately combining, in one application device, an active acid agent and an oil-in-water emulsion formed from lipid vesicles consisting of oily globules, each having a lamellar liquid crystal coating obtained from at least one surfactant, but which does not contain a gelling agent,
    wherein said composition has a pH of 2 to 4 and a viscosity greater than 500 centipoise.

27. A method of cosmetically treating the skin, comprising:
    applying the composition of claim 1 to the skin in order to tone it, to regenerate it, to smooth out the fine lines on the skin, and/or to combat the damage caused by UV radiation and/or to strengthen the skin tissues against attacking environmental factors.

28. A method of manufacturing a dermatological bleaching and/or depigmenting preparation, comprising:
    separately combining, in one application device, an active acid agent and an oil-in-water emulsion formed from lipid vesicles consisting of oily globules, each having a lamellar liquid crystal coating obtained from at least one surfactant, but which does not contain a gelling agent,
    wherein said composition has a pH of 2 to 4 and a viscosity greater than 500 centipoise.

* * * * *

UNITED STATES PATENT AND TRADEMARK OFFICE
CERTIFICATE OF CORRECTION

PATENT NO. : 6,416,768 B1  Page 1 of 1
DATED : July 9, 2002
INVENTOR(S) : Danielle Ravaux et al.

It is certified that error appears in the above-identified patent and that said Letters Patent is hereby corrected as shown below:

Column 10,
Line 20, delete "polyoxyechylenated" and insert -- polyoxethylenated. --

Column 11,
Line 17, delete "-" from "-butylmethoxydibenzoylmethane."

Signed and Sealed this

Twenty-eighth Day of January, 2003

JAMES E. ROGAN
*Director of the United States Patent and Trademark Office*